United States Patent
Schröder et al.

(10) Patent No.: US 11,780,803 B2
(45) Date of Patent: Oct. 10, 2023

(54) PROCESS FOR THE PREPARATION OF CYCLOPROPANE COMPOUNDS USING DIAZO-COMPOUNDS

(71) Applicant: Givaudan SA, Vernier (CH)

(72) Inventors: Fridtjof Schröder, Hettlingen (CH); Marcel Steck, Frauenfeld (CH)

(73) Assignee: GIVAUDAN SA, Vernier (CH)

( * ) Notice: Subject to any disclaimer, the term of this patent is extended or adjusted under 35 U.S.C. 154(b) by 445 days.

(21) Appl. No.: 16/973,591

(22) PCT Filed: Jun. 25, 2019

(86) PCT No.: PCT/EP2019/066849
§ 371 (c)(1),
(2) Date: Dec. 9, 2020

(87) PCT Pub. No.: WO2020/002338
PCT Pub. Date: Jan. 2, 2020

(65) Prior Publication Data
US 2021/0253514 A1    Aug. 19, 2021

(30) Foreign Application Priority Data
Jun. 27, 2018    (GB) ..................... 1810514

(51) Int. Cl.
*C07C 245/16* (2006.01)
*B01J 8/18* (2006.01)
*B01J 19/00* (2006.01)
*C07C 2/86* (2006.01)

(52) U.S. Cl.
CPC ............ *C07C 245/16* (2013.01); *B01J 8/1881* (2013.01); *B01J 19/0093* (2013.01); *C07C 2/86* (2013.01); *B01J 2208/00858* (2013.01); *B01J 2219/00867* (2013.01); *B01J 2219/00889* (2013.01); *C07C 2523/44* (2013.01); *C07C 2601/02* (2017.05)

(58) Field of Classification Search
CPC .................................................. C07C 245/16
See application file for complete search history.

(56) References Cited

U.S. PATENT DOCUMENTS

| 5,854,405 A | 12/1998 | Archibald et al. |
| 9,249,088 B2 | 2/2016 | Poechlauer et al. |
| 9,718,741 B2 | 8/2017 | Schröder et al. |
| 2014/0100360 A1 | 4/2014 | Poechlauer et al. |
| 2017/0283342 A1 | 10/2017 | Schröder et al. |

FOREIGN PATENT DOCUMENTS

| RU | 2417979 C2 | 5/2011 |
| WO | 2012128985 A1 | 9/2012 |
| WO | 2017046122 A1 | 3/2017 |

OTHER PUBLICATIONS

International Search Report for Application No. PCT/EP2019/066849 dated Sep. 27, 2019.
Written Opinion for Application No. PCT/EP2019/066849 dated Sep. 27, 2019.
Great Britain Search Report for Application No. 1810514.8 dated Jan. 31, 2019.
Michael Struempel, et al., Continuous Production of the Diazomethane Precursor N-Methyl-N-nitroso-p-toluenesulfonamide: Batch Optimization and Transfer into a Microreactor Setup, Organic Process Research & Development, Aug. 31, 2009, pp. 1014-1021, vol. 13, Issue 5, American Chemical Society.
Roda N. M., et al., Cyclopropanation using flow-generated diazo compounds. Organic & Biomolecular Chemistry, Jan. 7, 2015, vol. 13, No. 9, pp. 2550-2554. Schemes 1 and 3-4, Table 1.
Intellectual Property Office of Singapore Search Report for App. No. 11202011687R dated Dec. 4, 2022.
Intellectual Property Examination Report, Government of India for App.No. 202047055979 dated Jun. 20, 2022.
Brazilian Patent Office Search Report for App. No. BR112020023769-8 dated Feb. 23, 2023. English machine translation of pp. 3 and 4 are attached.
Loebbecke, et al. "Microreactors for Processing of Hazardous and Explosive Reactions." IChemE Symposium Series, No. 153. 2007.

*Primary Examiner* — Golam M Shameem
(74) *Attorney, Agent, or Firm* — Curatolo Sidoti & Trillis Co., LPA; Floyd Trillis, III; Salvatore A. Sidoti

(57) ABSTRACT

A process for the continuous production of a reaction product of a diazo-compound and a substrate in a multi-stage flow reactor is disclosed.

19 Claims, 4 Drawing Sheets

PROCESS FOR THE PREPARATION OF CYCLOPROPANE COMPOUNDS USING DIAZO-COMPOUNDS

CROSS REFERENCE TO RELATED APPLICATIONS

This application is a national stage application of International Application No. PCT/EP2019/066849, filed 25 Jun. 2019, which claims priority from Great Britain Patent Application No. 1810514.8 filed 27 Jun. 2018, both of which applications are incorporated herein by reference in their entireties.

FIELD OF THE INVENTION

The present invention is concerned with improved methods and apparatus for the production and further conversion of diazo-compounds.

BACKGROUND OF THE INVENTION

The diazo-compound, diazomethane, is a highly reactive gas with a wide range of uses in chemical syntheses. In particular, it has been used in cycloaddition reactions with olefins to form cyclopropanes. Unfortunately, diazomethane is also an explosive, a powerful carcinogen, as well as being allergenic and toxic, and it is the difficulty regarding the issue of its safe handling that affects its wider adoption in large-scale synthesis of industrially useful compounds.

The prior art addresses issues related to the safe handling of diazo-compounds, such as diazomethane, in synthetic organic chemistry. In particular, Poechlauer in U.S. Pat. No. 9,249,088 describes a process for the continuous formation and continuous reaction of diazo compounds. Poechlauer, more specifically, describes a flow process in which a precursor compound of diazomethane (such as N-methyl-N-nitroso urea) is continuously formed and continuously converted into diazomethane in the presence of a base. The diazomethane in a solvent is continuously removed from the reactor in which it is formed through a hydrophobic membrane and fed into a second flow reaction chamber. The second flow reaction chamber contains a substrate that is reactive with the formed diazomethane, and the substrate and diazomethane react to form a desired reaction product.

According to Poechlauer, this continuous process ensures that only relatively low levels of diazomethane (as well as its precursor compounds, which are also toxic) are formed in the flow reactor. This represents an improvement over prior art batch processes that involve the formation of large standing concentrations of diazomethane (as well as its precursor compound). Nevertheless, a problem with the Poechlauer approach is that it teaches the formation of diazomethane in a first reactor and its transfer into a second reactor, across a membrane, where it reacts with a substrate provided therefor. In other words, this process necessarily involves the formation of a concentration of hazardous diazomethane on one side of a membrane, and a mass transfer of diazomethane across the membrane, which will not be instantaneous, and even less so should the passage across the membrane become blocked or hindered for any reason.

Furthermore, the interposition of a membrane between the formed diazomethane (as well as its precursor compound) in a first reactor and the substrate with which it is intended to react in a second reactor, also creates process engineering complexity in that a balance must be achieved with regard to the rates at which the diazomethane is formed, and passes across the membrane, and the rate at which it reacts with the substrate once it has crossed the membrane, in order that it is completely consumed rather than being discharged from the reactor in an unreacted form.

There remains a need to provide an improved process for the continuous formation of a diazo compound, and in particular diazomethane, and its continuous reaction with a suitable substrate, such as an olefin, in order to ensure good conversion of the diazo compound and concomitantly very high yields of desired reaction product. Ideally the diazo compound precursor as well as the diazo compound itself should be quantitatively converted to avoid contamination of the desired reaction product by these reactants. An improved process is also needed to ensure the safe handling of diazo compounds and their precursor compounds by ensuring that whilst the total inventory of a diazo compound/precursor produced during the course of a given reaction necessarily may be within an hazardous level, nevertheless, at no given point of time, or in any region or stage of a reactor does the concentration of the diazo compound/precursor compound reach an unsafe and/or explosive level.

SUMMARY OF THE INVENTION

The applicant has addressed the deficiencies in the prior art and provides, in accordance with the invention, a process whereby a diazo compound, such as diazomethane, is continuously formed, and then consumed by a substrate in a multistage continuous flow reactor to produce a reaction product of the diazo compound and substrate that can be discharged from the multistage continuous flow reactor devoid of any hazards associated with the presence of the diazo compound, and during which reaction the diazo compound is both formed and further reacted with a substrate in the same reaction chamber thereby to produce said reaction product.

Accordingly, the invention provides in a first aspect a process for the continuous production of a reaction product of a diazo-compound and a substrate (so-called "diazo reaction product") in a multistage continuous flow reactor comprising at least two connected reactors (also referred to as reaction chambers) in fluid communication with each other, wherein a reaction product formed at each stage of the multistage sequence is continuously discharged from an upstream reactor (or upstream reaction chamber) in which it is formed, and is fed as a continuous fluid stream into a downstream reactor (or downstream reaction chamber) whereupon it can undergo further conversion, the process being characterized in that a precursor compound of the diazo compound that is continuously formed in an upstream reactor (upstream reaction chamber), is continuously discharged from the upstream reactor (upstream reaction chamber) into a downstream reactor (downstream reaction chamber) under conditions conducive to convert it into the diazo compound, and wherein said downstream reactor (downstream reaction chamber) contains the substrate with which the diazo compound reacts to form the diazo reaction product.

Furthermore, in another aspect the invention provides apparatus, which is a multistage continuous flow reactor, suitable for carrying out the process described hereinabove.

DETAILED DESCRIPTION OF THE INVENTION

An advantage of the present invention resides in the use of a substrate essentially as a quenching medium that is contained in the same reaction chamber in which the diazo compound is formed. In this way, it is ensured that substantially immediately after the diazo compound is formed, it will be consumed by the substrate to form the diazo reaction product. This ensures that whereas large quantities of diazo compound will be formed over the entire course of the continuous reaction, at no given point in time, and at no location in the reaction chamber or the multistage continuous flow reactor will hazardous concentrations of the diazo compound be present.

Diazo compounds useful in the present invention can be any compound having two linked nitrogen atoms as a terminal functional group. Simple forms of these compounds include diazomethane, diazoethane or diazoacetate which are all useful as reagents in the present invention, diazomethane being of use in particular.

Suitable substrates that are employed to react with diazo compounds and form the desired diazo reaction product include olefins, aldehydes, ketones, cyclic ketones, carboxylic acids and the like. Of particular interest as substrates in the present invention are olefins, and more particularly di-olefins or poly-olefins, preferably having at least one terminal (mono-substituted) double bond. Particularly useful olefins are described in U.S. Pat. No. 9,718,741, which is herein incorporated by reference, and include more particularly polyprene type olefins such as isoprene, myrcene, farnesene and β-springene (a diterpenoid analogue of farnesene), in particular farnesene.

Diazo compound precursors are well known in the art, and typically include N-alkyl-N-nitroso compounds. The alkyl group is typically methyl, but can include the ethyl analog or even higher alkyl analogs, such as propyl, butyl and so on, which may be linear or branched and may be substituted or unsubstituted. Particularly useful precursor compounds include but are not limited to N-methyl-N-nitroso urea (MNU), N-methyl-N-nitroso-p-toluenesulfonamide (Diazald), methyl methyl(nitroso)carbamate, ethyl methyl(nitroso)carbamate, and N-methyl-N-(2-methyl-4-oxopentan-2-yl)nitroso amide (Liquizald), with Liquizald representing a particularly preferred precursor compound.

N-alkyl-N-nitroso precursor compounds referred to hereinabove are typically formed when a corresponding N-alkyl compound, such as an alkyl amine or a derivative of an alkyl amine, such as methyl urea, is converted into a nitroso derivative by the action of an aqueous solution of nitrite ions, such as sodium nitrite, and an organic or a mineral acid.

Examples of N-alkyl compounds or derivatives thereof are commercially available or can be prepared from commercially available starting materials. Particular N-alkyl compounds include but are not limited to N-methylurea, N-methyl-toluolsulfonylamide, ethyl methylcarbamate, and 4-methyl-4-(methylamino)pentan-2-one, in particular 4-methyl-4-(methylamino)pentan-2-one.

The process of the present invention is a continuous process, by which is meant that the process involves feeding one or more continuous fluid streams containing reagents, reactants, solvents or the like through tubes into a reactor (or reaction chamber), such that where said fluid streams contact each other chemical reactions can take place, and the reaction products formed can be continuously discharged in a fluid stream, optionally to be passed into further connected reactors (or reaction chambers). This is to be contrasted with a batch-type reaction, in which significant volumes of a reaction mixture or reaction product are held in a reaction vessel until at a moment of choosing, the reaction mixture or reaction products can be discharged.

Furthermore, the process according to the present invention may be run as a multi-stage reaction, by which is meant that the diazo reaction product is formed by means of a plurality of successive reaction stages, wherein during each stage of the reaction, a reaction product, formed in a preceding stage, is discharged from the reactor (or reaction chamber) in which it is produced and fed into a successive reactor (reaction chamber) as a reactant, thereby to undergo further chemical conversion, this process being repeated until the diazo reaction product is produced.

The process according to the present invention may be carried out in any form of reactor that is set-up for continuous flow conditions. Continuous flow reactors, such as microreactors, in particular, are useful in accordance with the present invention. A microreactor is essentially a miniaturized flow reactor, usually in tubular form, most often with the tubes arranged on or within a chip, having characteristic tube diameters measured in micrometers up to about 1 mm. Such reactors are well known in the art and require no detailed description herein, but it is well understood that, especially when upscaling is considered, the diameters of the tubes can be increased to millimeters if not even centimeters to allow an increased throughput of the reagents, reaction partners, solvents and reaction products. Within these dimensions simply the general term of "flow reactor" is used, with all possibilities of fine structures or arrangement of the corresponding tubes. Alternatively more than one and in principle an unlimited number of microreactors can be operated in parallel, this also enhances the theoretical diameter of the original single microreactor tube (so-called "outscaling").

Reagents, reactants, solvents, or the like, intended to be introduced in a particular stage of a multi-stage reaction may be mixed together to form a fluid stream by means of feeder tubes and T-connectors, which mixtures may then be further transported as a single or multi fluid feed streams into further tubes or flow reactors (or reaction chambers) wherein reactions can occur, with the corresponding reaction products being continuously discharged through an outlet of the reactor (or reaction chamber). The terms "reactor" and "reaction chamber" are interchangeable. Both describe parts of the overall multistage continuous flow reactor.

In a multi-stage process, a multistage continuous flow reactor comprises at least two reactors or reaction chambers, more particularly at least three reactors or reaction chambers, and still more particularly at least four or more reactors or reaction chambers, which are connected and in fluid communication with each other, and into and through which a directed flow can be applied. Reactors or reaction chambers are each equipped with inlets and outlets for feeding and discharging a fluid stream of reagents and reaction products respectively, and the reactor or reaction chamber defines an internal volume in which reagents, reactants, solvents and the like react to form successive reaction products.

The feeder tubes and T-connectors may be assembled in such a way as to control the manner in which reagents, reactants, solvents or the like are mixed, fed and discharged, both temporally and spatially, in order to control or optimize reaction conditions such as temperature, pressure as well as to control composition of mixtures, thereby ensuring that successive reaction products are formed in an optimized manner. A process in which one or more reactants, reagents, solvents or the like is fed into a reaction chamber in an optimized temporal and distributed fashion in order to meet safety and performance requirements, is a particular object of the present invention.

The process according to the present invention is particularly suitable for effecting the addition of diazomethane to an olefin substrate to provide a diazo reaction product containing a cyclopropane functional group formed by the action of diazomethane on an olefinic double bond on the substrate.

Accordingly, in a particular aspect of the present invention, there is provided a continuous process of producing a cyclopropanated compound, the process comprising the steps of:

Providing a multistage continuous flow reactor comprising at least two, more particularly at least three, and more particularly still at least four or more connected reaction chambers in fluid communication with each other;

At each stage of the reaction, continuously feeding a fluid stream of reactants, reagents, solvents or the like, in a directed flow into a reaction chamber under conditions conducive to form a reaction product;

Continuously discharging from that reaction chamber a fluid stream of reaction product, and feeding it into a successive reaction chamber there to undergo further conversion to form a successive reaction product; characterized in that a diazomethane precursor compound formed as a reaction product in a reaction chamber is continuously discharged from that reaction chamber (upstream reactor) and continuously fed into a successive reaction chamber (downstream reactor) under conditions conducive to convert the precursor compound into diazomethane, and wherein said successive reaction chamber contains an olefin-containing substrate with which the diazomethane reacts to form the desired cyclopropanated compound.

In an embodiment of the present invention, the process of forming the cyclopropanated compound comprises the step of feeding a continuous fluid stream of a reaction mixture comprising an organic phase containing mesityl oxide and an aqueous phase comprising alkyl amine into a first reaction chamber under conditions conducive to form the N-alkyl compound derivative such as a 4-(alkylamino)-4-methylpentan-2-one, or in particular 4-methyl-4-(methylamino) pentan-2-one as a reaction product.

In an embodiment of the present invention, an organic phase comprising an N-alkyl compound derivative, such as a 4-(alkylamino)-4-methylpentan-2-one, and for example 4-methyl-4-(methylamino) pentan-2-one, formed in a first reaction chamber, is mixed with an acid and an aqueous phase containing nitrite ions to form a reaction mixture, and a continuous stream of this reaction mixture is fed into a successive reaction chamber downstream of the first reaction chamber under conditions conducive to form as a reaction product the diazomethane precursor N-methyl-N-(2-methyl-4-oxopentan-2-yl) nitrous amide (also known as Liquizald).

In an embodiment of the present invention, an organic phase comprising N-methyl-N-(2-methyl-4-oxopentan-2-yl) nitrous amide (Liquizald) formed in a reaction chamber and separated by phase separation from an aqueous phase, is mixed with an olefin substrate, a palladium catalyst and an aqueous phase containing a suitable base in a successive reaction chamber under conditions conducive to the formation of diazomethane, and wherein the diazomethane formed reacts with the olefin substrate to form a cyclopropanated compound, which is discharged as a continuous fluid stream from the reaction chamber.

The following figures serve to further illustrate the invention or specific aspects of the invention:

Figure 3:
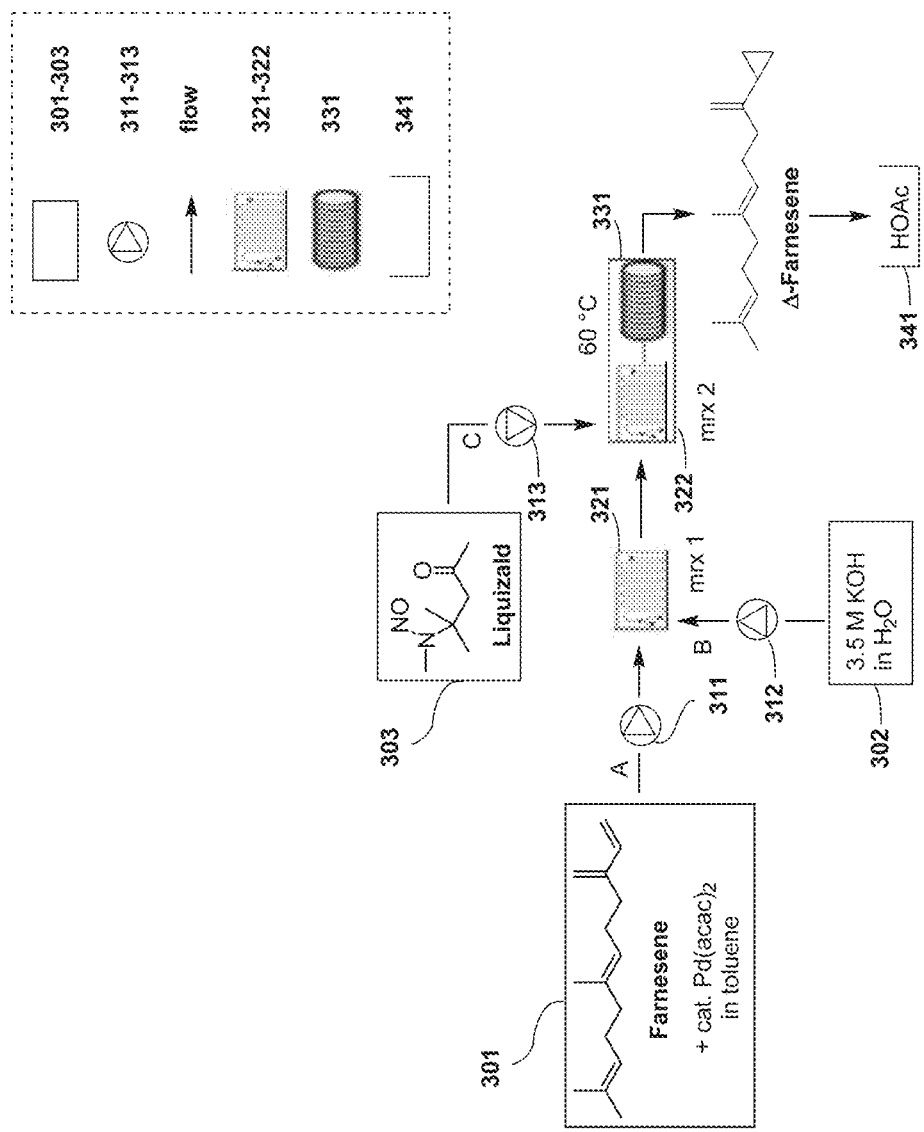
Figure 4:
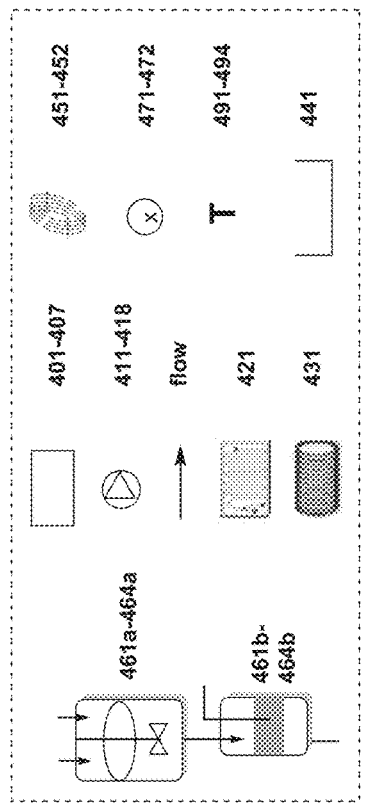
Figure 4:
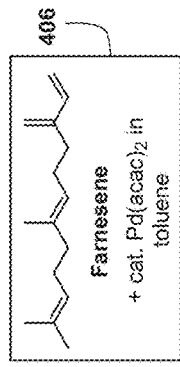
Figure 4:
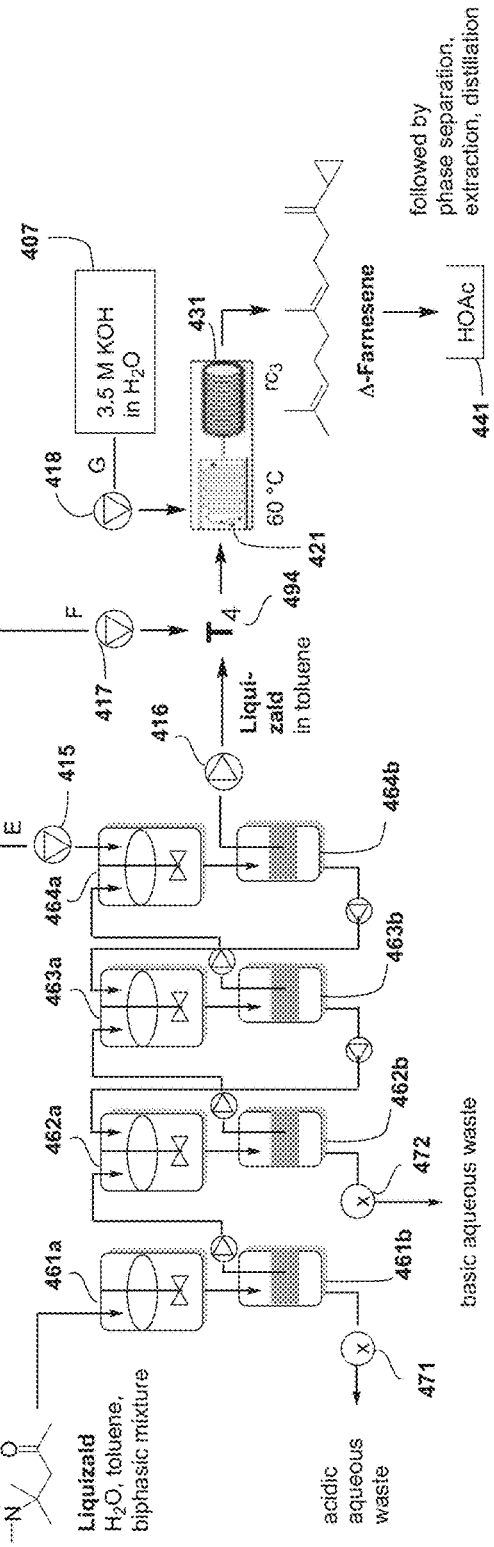

FIG. 3 shows a schematic representation of an alternative reaction chamber in which the diazo reaction product is formed, and a batch-related addition mode of the reagents is applied in the flow process; and FIG. 4 shows a schematic representation of an alternative multistage continuous flow reactor, suitable for a process for the continuous production of a "diazo reaction product", further comprising multiple Continuously Stirred Tank Reactors (CSTRs) and biphasic settlers.

In the process of converting a precursor compound (e.g. Liquizald) into diazomethane and further into the diazo reaction product, the sequence of addition of reactants and reagents is of particular importance. When such a synthetic step is carried out as described in prior art batch processeses, (e.g. as in WO 2015059290), Liquizald in a suitable organic solvent, such as toluene, is added to a vigorously stirred biphasic mixture comprising a substrate containing an olefinic double bond, such as farnesene, a suitable catalyst, e.g. $Pd(acac)_2$ and a base, e.g. KOH. A representative example of such a batch process is set out in the examples (see Example 1). However, adopting this addition sequence in the method of the present invention using continuous flow is problematic. More particularly, it creates additional complexity in the apparatus set-up, which requires a greater number of pumps and microreactors owing to the need for pre-mixing and pumping of the biphasic mixture before the addition of Liquizald. Furthermore, the reaction results in a much lower conversion of substrate, which can possibly be attributed to the pumping of inhomogeneous mixtures and poor phase mixing in the reactor. This is further demonstrated in the Examples, and more particularly Examples 7 and 8 which are representing a set up according to FIG. 3, as well as a comparison of FIGS. 2 and 3.

Figure 1:
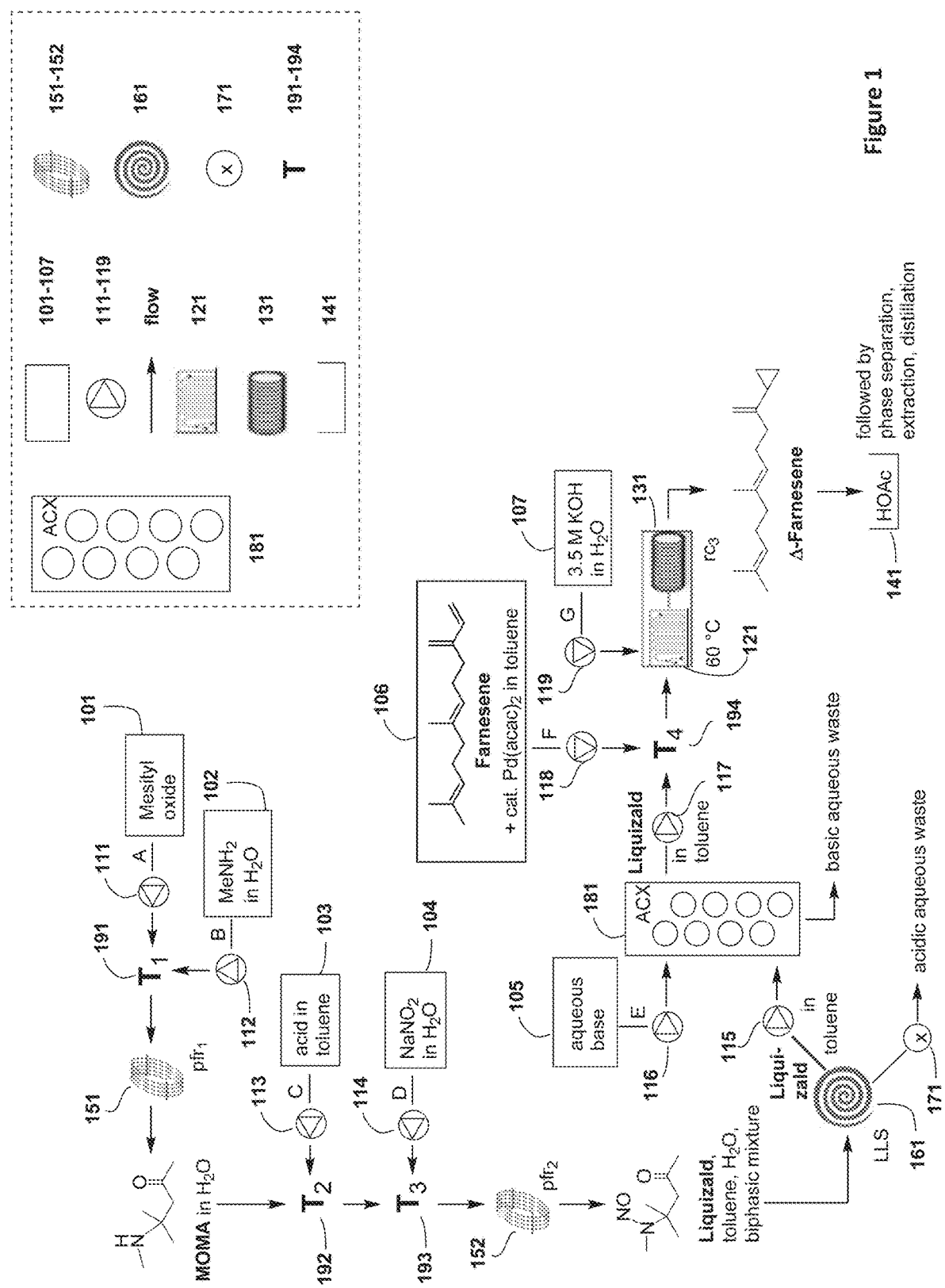
FIG. 1 shows a schematic representation of a multistage continuous flow reactor suitable for a process for the continuous production of a "diazo reaction product"
Figure 2:
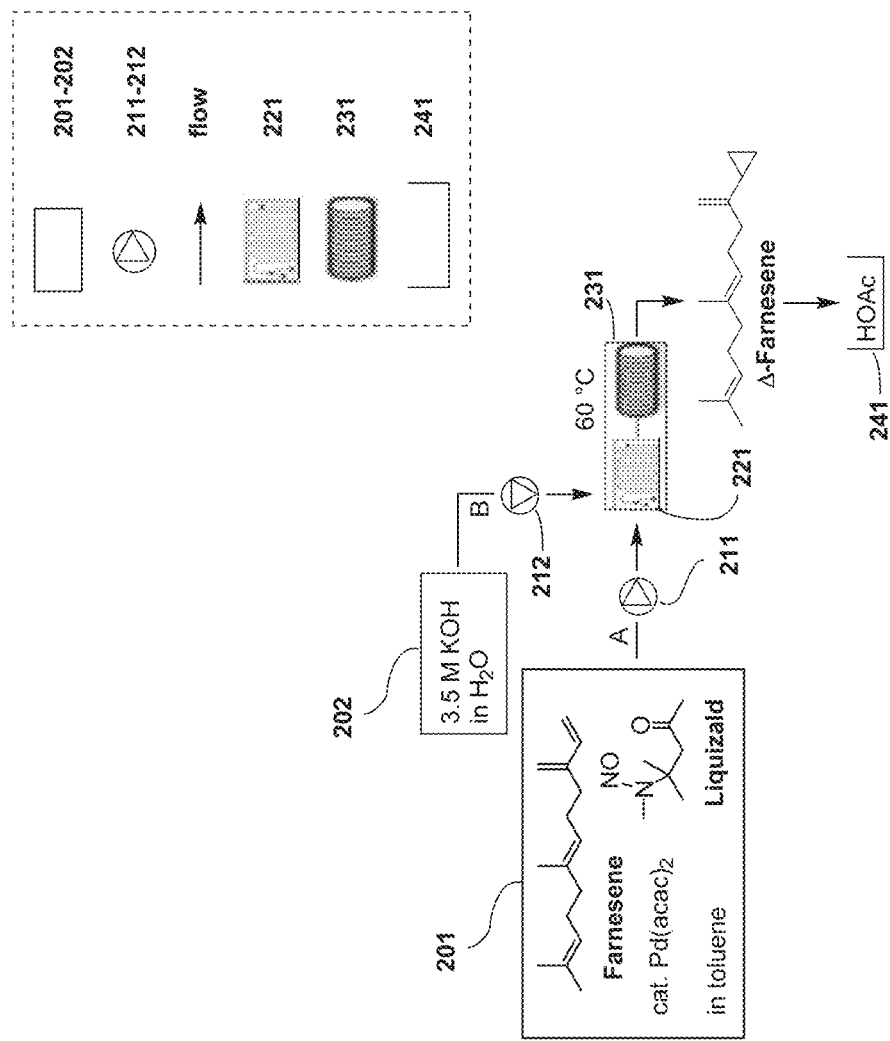
FIG. 2 shows a schematic representation of a reaction chamber in which the diazo reaction product is formed, and a new addition mode of the reagents is applied in the flow process.

An addition sequence wherein an aqueous phase (e.g. KOH in water) and an organic phase ($Pd(acac)_2$, Liquizald and Farnesene in toluene) are continuously mixed, was found to be much more efficient and simple regarding optimizing conversions and technical set-up (FIG. 2). An example of this reaction in a single microreactor, which corresponds to a reactor or a reaction chamber, and residence unit is set-forth in Example 2. FIG. 2 illustrates the arrangement of the last reaction chamber in FIG. 1 or FIG. 4, in which the diazo reaction product is formed, but can also be regarded as an independent continuous flow reactor.

Steps in the multi-stage process of forming a cyclopropanated compound described hereinabove may be carried out in a biphasic medium comprising an organic and aqueous phase. By way of example, after formation of 4-methyl-4-(methylamino)pentan-2-one, the successive reaction products formed during each stage of the process are soluble or dispersible in an organic phase. Therefore, if it is desired, aqueous-soluble or dispersible effluents or by-products can be continuously separated from the organic phase by means of phase separation techniques.

Separation of the precursor compound—Liquizald—from the aqueous phase is of particular importance because Liquizald is formed under acidic conditions, whereas the formation of diazomethane from Liquizald is carried out in a biphasic mixture under basic conditions. Accordingly, before Liquizald is continuously fed into a reaction chamber to form diazomethane, it is desirable to separate the Liquizald-containing organic phase from the aqueous phase by suitable phase separation means, and it is furthermore beneficial before the subsequent synthetic step is undertaken, to remove traces of acid from the Liquizald-containing phase by washing it with portions of a suitable aqueous base.

Phase separation and washing with aqueous base can be carried out under continuous flow conditions by passing the biphasic reaction mixture containing the precursor compound (e.g. Liquizald) through a continuous extraction apparatus, such as Continuously Stirred Tank Reactors (CSTRs). The use of counter current extraction in multistep flow sequences is described for example by K. P. Cole et al. in Science 356, 1144-1150 (2017). Ideally CSTRs are miniaturized to decrease the volumes of Liquizald during extraction and washing, which can be done for example with liquid-liquid separators (LLS) and agitated cell extractors (ACX), which decrease the stationary amount of Liquizald, and feeding the Liquizald-containing phase into a successive reactor for the cyclopropanation step. The principle of using liquid-liquid separators (LLS) is described for example in technical notes from companies such as Zaiput Flow Technologies or in multistep flow publications which describe the use of such LLS, see for example J. Britton, C. L. Raston, *Chem. Soc. Rev.* 46, 1250-1271 (2017). The principle of using agitated cell extractors for counter-current extraction is generally well known in the art, and described for example in technical notes from companies such as AM Technology or in reviews describing the principles of such techniques, see for example F. Visscher, J. van der Schaaf, T. A. Nijhuis, J. C. Schouten, *Chemical Engineering Research and Design* 91, 1923-1940 (2013).

FIG. 1 depicts a schematic representation of a process and apparatus for the continuous production of a cyclopropanated compound in accordance with a particularly preferred embodiment of the invention, which Figure and description serve to further describe the invention. The description refers, for sake of simplicity, to the continuous synthesis of Liquizald and its use for the cyclopropanation of Farnesene, but any other precursor compound, such as any N-alkyl-N-(2-methyl-4-oxopentan-2-yl)nitrous amide precursor can be made and any other alkene substrate used for cyclopropanation. The following elements are arranged in FIG. 1: reservoirs 101-107, pumps 111-119, flow in tube represented by arrows, microreactor 121, residence coil with static mixture 131, quenching vessel 141, plug flow reactors 151-152, liquid-liquid separator LLS 161, back pressure regulator 171, agitated cell extractor (ACX) 181, T-connections 191-194. With reference to FIG. 1:

- in a first step mesityl oxide (from reservoir 101, through feed A, pump 111) and methyl amine (from reservoir 102, through feed B, pump 112) are mixed in a T-piece (191, $T_1$) and a plug flow reactor (151, $pfr_1$) in which these components react to produce 4-methyl-4-(methylamino)pentan-2-one (MOMA=Mesityl Oxide/Methyl Amine adduct);
- in a second and third step an acid in toluene (from reservoir 103, through feed C, pump 113) and sodium nitrite in water (from reservoir 104, through feed D, pump 114) are added in two subsequent T-pieces (192, $T_2$ and 193, $T_3$) whereupon these components react to provide N-methyl-N-(2-methyl-4-oxopentan-2-yl) nitrous amide (Liquizald) in the third T-piece (193, $T_3$) and a subsequent plug flow reactor (152, $pfr_2$). Alternatively sodium nitrite can be added first, then the acid;
- in a fourth and fifth step the resulting biphasic mixture from step 3 is separated by a liquid-liquid separator (161, LLS, step 4), the acidic aqueous waste is removed (passing a back pressure regulator 171). The organic phase moves forward (pump 115), and residual acid is removed by continuous washing (step 5) in an agitated cell extractor (181, ACX), to which aqueous base is added (from reservoir 105, through feed E, pump 116);
- in a sixth step the organic layer containing Liquizald is pumped (pump 117) into a T-piece (194, $T_4$) where it is mixed with the polyene substrate (Farnesene) and catalyst in toluene (from reservoir 106, through feed F, pump 118);

The resulting Liquizald-containing mixture is pumped into a microreactor (121) where it is mixed in a seventh step with aqueous base (from reservoir 107, through feed G, pump 119), whereupon the cyclopropananation product is formed in the microreactor 121 and a subsequent residence coil 131. The resulting cyclopropanated product mixture is directed from the residence coil into a vessel 141 containing a quench solution where the biphasic mixture is permitted to settle. The quench-solution is used for safety reasons. In case of fully converted Liquizald and diazomethane quenching is not necessary.

After step seven the biphasic mixture comprises the cyclopropanated compound (the diazo reaction product) in an organic phase and an aqueous phase containing a waste mixture, which can be separated by normal batch-wise separation because reaction parameters can be adjusted to ensure that this mixture does not contain any unreacted Liquizald and/or diazomethane. Optionally it is of course possible to continue with the work-up and purification of the product under flow conditions.

There now follows a series of examples that serve to further illustrate the invention. The following examples are given to illustrate preferred embodiments of the invention. It will be understood that these examples are illustrative and the invention is not to be considered as restricted thereto.

General:

Non-polar GC condition: 100° C., 1 min, 20° C./min to 240° C., 5 min, 240° C. GC Agilent 7890B Series GC system. Non-polar column: HP-5 from Agilent Technologies, 0.32 mm×0.25 mm×30 m. Carrier gas: hydrogen. Injector temperature: 230° C. Split 1:50. GC calibration with Liquizald 80% (as determined by NMR) and decane. rpa %=relative peak areas.

Non-polar GCMS-conditions: 50° C., 2 min, 20° C./min to 240° C., 35° C./min to 270° C. GCMS Agilent 5975C MSD with HP 7890A Series GC system. Non-polar column: BPX5 from SGE, 5% phenyl 95% dimethylpolysiloxan 0.2 mm×0.25 mm×12 m. Carrier gas: helium. Injector temperature: 230° C. Split 1:50. Flow: 1.0 ml/min. Transfer line: 230° C. MS-quadrupol: 150° C. MS-source: 230° C. rpa %=relative peak areas.

Example 1 (Comparative)

The cyclopropanation reaction under batch conditions is set forth hereinbelow:

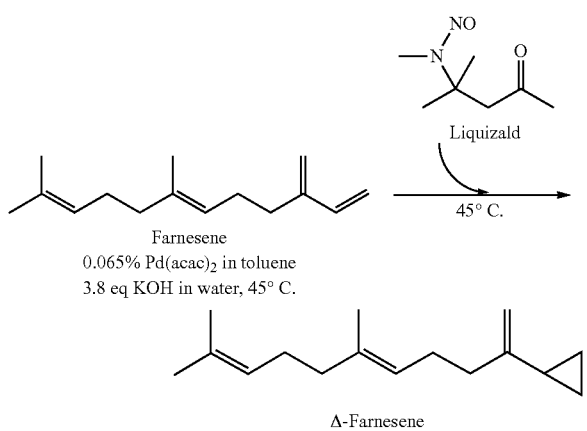

Liquizald 46% in toluene (18.3 g, 53 mmol, 1.7 eq) is added at 45° C. and over 2 h to a stirred biphasic mixture of Farnesene 98% (6.4 g, 31 mol) and Pd(acac)$_2$ (6.3 mg, 20 µmol, 0.065%) in toluene (27 ml) and KOH (8 g, 0.12 mol) in water (34 ml). After 30 min at 45° C. and complete conversion as detected by GC the reaction mixture is poured upon acetic acid (25 ml). After phase separation the organic phase is washed with water, dried over MgSO$_4$, filtered, and the solvents are evaporated. The brown orange oil (7 g) contains 92% Δ-Farnesene, 8% of Δ$_2$-Farnesene according to GC which corresponds with a GC-calibrated purity (84%) of Δ-Farnesene to a corrected yield of 86% Δ-Farnesene based on Farnesene.

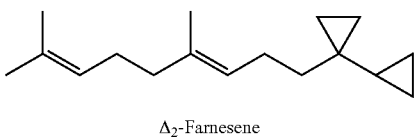 [SMILES: CC(C)=CCC/C(C)=C/CCC1(C2CC2)CC1]

Δ$_2$-Farnesene

Example 2

Cyclopropanation reaction under flow conditions and new addition mode with 0.065% Pd(acac)$_2$, as set forth in FIG. 2.

Equipment: Sigma-Aldrich Microreaction Explorer Kit No. 19979-1kt, © 2007, Version 1.02, Sigma Aldrich Production GmbH, Buchs, Switzerland. Microreaction plate: MR #437383, Little Things Factory, Volume 0.7 ml, PTFE tube, borosilicate glass, ceramics, max. inner pressure 6.5 bar. Two 100 ml round bottom flasks. 200 ml sulfonation-flask with acetic acid as quench. One gas washing bottle with acetic acid and one safety bottle. Two Ismatec pumps. Residence coil: 1.25 m stainless steel tube, 5 mm inner diameter, 18 ml volume, filled with 19 static polypropylene mixers. The self-made residence unit is described in the bachelor work of Fabian Ruethi ("TPO continuously for Silvanone", page 72 and 124, Zürcher Hochschule für Angewandte Wissenschaften, 2012): 1.25 m stainless steel tube, 5 mm inner diameter, 18 ml volume, filled with 19 static mixers. Static mixers: 6.5 mm length, 4.8 mm diameter. Pumps, the microreactor and the residence coil are connected by teflon tubings with 1.5 mm inner diameter.

Feed A: Farnesene of 98% purity (6.4 g, 31 mmol), Pd(acac)$_2$ (6.3 mg, 0.02 mmol. 0.065 mol %) in toluene (5 ml) [Note 1], and Liquizald 33% in toluene (25.7 g, 53.6 mmol, 1.7 mol-eq) pre-mixed in toluene (13 ml) pumped with 3.4 ml/min into microreactor and residence unit. Feed B: 3.5 M aqueous KOH (34 ml, 117 mmol) pumped with 2.2 ml/min into microreactor and residence unit.

Feed A (from reservoir 201) and feed B (from reservoir 202) are pumped (pumps 211 and 212) through the set-up of FIG. 2 into microreactor 221 and residence coil 231 in an oil bath heated to 75° C. outer and at 70-60° C. inner temperature [Note 2]. The product flow (5.6 ml/min, residence time 3.3 min in microreactor and residence unit) is quenched (in vessel 241) sub-surfacely and under cooling (at 10-20° C. inner temperature to avoid solidification of HOAc) through acetic acid (15 g, 0.25 mol) [Note 3]. The biphasic quench mixture is transferred to a separation funnel, the phases are separated, and the organic phase is washed with water (100 ml), dried over MgSO$_4$ (30 g), filtered and evaporated under reduced pressure. Crude Δ-Farnesene (6.9 g) is obtained as brown oil with a purity of 82.5%, as determined by GC- and NMR-calibration [Note 4]. GCMS of this material indicates a quantitative conversion to Δ-Farnesene (92% rpa) and Δ$_2$-Farnesene (8% rpa) and the absence of Liquizald. Yield of Δ-Farnesene from Farnesene (corrected by purity): 84% [Note 4]. The analytical data of Δ-Farnesene and Δ$_2$-Farnesene were identical with the ones described in WO 2015059290.

Notes:

[1] The catalyst Pd(acac)$_2$ is soluble in toluene.

[2] Sensor in the microreactor not connected with the reaction stream.

[3] Pure HOAc was used because complete cyclopropanation in the microreactor had to be proven and possible post-reactions in the quenching vessel had to be excluded. Excess HOAc (2×molar excess over KOH used) guaranteed non-basic quench conditions. Nitrogen is produced in the microreactor by controlled decomposition of the diazomethane and is led from the quench vessel through a washing bottle filled with pure HOAc. Only traces of MeOAc (~0.02%) were detected in the washing bottle by NMR and only after several similar optimization experiments using the same washing bottle. The quench-solution can be applied for safety reasons. In case of fully converted Liquizald and diazomethane, quenching is not necessary.

[4] The content of Δ-Farnesene was determined by NMR- and GC-calibration to 82.5%.

A comparison of Example 1 (batch reaction) and Example 2 (flow reaction) shows that under otherwise identical conditions yields and purities are (within an error of 2%) similar under batch and flow conditions.

Example 3

The flow reaction described in Example 2 was repeated under nearly identical conditions and in the same equipment but without residence unit:

Feed A: Farnesene of 98% purity (6.76 g, 32 mmol), Pd(acac)$_2$ (6.5 mg, 21 µmol, 0.065 mol %) and Liquizald 38% in toluene (23.34 g, 55.3 mmol, 1.7 mol-eq) pre-mixed in toluene (18 ml) pumped with 1.7 ml/min into the microreactor without residence unit. Feed B: 3.5 M aqueous KOH (33 ml, 114 mmol) pumped with 1 ml/min into the microreactor without residence unit.

Feed A and feed B are pumped (as described in example 2 subsequent but without residence coil) into the microreactor in an oil bath heated to 75° C. outer and at 70-60° C. inner temperature. The product flow (2.7 ml/min, residence time 15 sec in the microreactor) is quenched sub-surfacely and under cooling (at 10-20° C.) through acetic acid (15 g, 0.25 mol). A GC taken 30 min after completed quench shows Liquizald (26%), Farnesene (67%) and Δ-Farnesene (7%).

This experiment shows that a 20-fold reduced residence time due to the absence of a residence unit drastically reduces the conversion of Farnesene and Liquizald to Δ-Farnesene.

Example 4

The flow reaction described in Example 2 was run with 1.2 mol-eq Liquizald (instead of 1.7 mol-eq versus Farnesene):

Feed A: Farnesene of 98% purity (8.96 g, 43 mmol), Pd(acac)$_2$ (8.8 mg, 0.03 mmol) and Liquizald 40% in toluene (20.8 g, 52.6 mmol) pre-mixed in toluene (22 ml) pumped with 3.4 ml/min into microreactor and residence unit. Feed B: 1.75 M aqueous KOH (23 ml, 40 mmol) pumped with 1.4 ml/min into microreactor and residence unit.

Feed A and feed B are pumped through the set-up of FIG. 2 into microreactor and residence coil in an oil bath heated to 75° C. outer and at 70-60° C. inner temperature. The product flow (4.8 ml/min, residence time 4 min) is quenched sub-surfacely and under cooling (10-20° C.) through acetic acid (15 g, 0.25 mol) [Note 3]. The biphasic quench mixture is transferred to a separation funnel, the phases are separated and the organic phase is washed with water (100 ml), dried over MgSO$_4$ (30 g), filtered and evaporated under reduced pressure. Crude Δ-Farnesene (11.6 g) is obtained as brown oil with a purity of 66%, as determined by GC- and NMR-calibration]. GCMS of this material indicates a 91% conversion to Δ-Farnesene (85% rpa) and Δ$_2$-Farnesene (6% rpa) and the absence of Liquizald. Yield of Δ-Farnesene from Farnesene (corrected by purity): 82%.

In comparison with example 2 this result shows that with less Liquizald (Liquizald/Farnesene ratio 1.2 instead of 1.7) the conversion of Farnesene is still extensive, and that the corr. yield of Δ-Farnesene (82%) is still comparable to the one obtained using more (1.7 eq) Liquizald (84% in example 2). It must be mentioned at this point that incomplete conversions are rather acceptable than over-cyclopropanation to Δ$_2$-Farnesene because the bis-cyclopropanated byproduct cannot be recycled, whereas unconverted Farnesene can be, after distillative separation from Δ-Farnesene, recycled as substrate.

Example 5

The flow reaction described in Example 2 was run with 0.02% catalyst (instead of 0.065% catalyst).

Feed A: Farnesene of 98% purity (6.48 g, 31 mmol), Pd(acac)$_2$ (2 mg, 6.4 μmol) and Liquizald 43% in toluene (19.8 g, 54 mmol, 1.7 eq) pre-mixed in toluene (24 ml) pumped with 1.7 ml/min into microreactor and residence unit. Feed B: 3.55 M aqueous KOH (34 ml, 120 mmol) pumped with 1.1 ml/min into microreactor and residence unit.

Feed A and feed B are pumped as described in example 2 and FIG. 2 into microreactor and residence coil. Total Flow: 2.8 ml/min. Residence time: 6.5 min. The product flow is quenched subsurfacely through acetic acid. A GC taken 30 min after complete quench indicates a 82% conversion to Δ-Farnesene (77% rpa) and Δ$_2$-Farnesene (4% rpa) and the absence of Liquizald.

This example shows that at much lower catalyst concentration (0.02 instead of 0.065 mol %) still acceptable conversions are obtained in flow.

Example 6

The flow reaction described in Example 5 was run in batch mode.

Liquizald 37% in toluene (23.1 g, 53 mmol, 1.7 eq) is added at 45° C. and over 2 h to a stirred biphasic mixture of Farnesene 98% (6.4 g, 31 mol) and Pd(acac)$_2$ (2 mg, 6.3 μmol, 0.02%) in toluene (27 ml) and KOH (8 g, 0.12 mol) in water (34 ml). A GC taken 30 min after complete quench indicates a 78% conversion to Δ-Farnesene (70%), Δ$_2$-Farnesene (4%) and another monocyclopropanated byproduct (2%).

A comparison of the results from batch (example 6) and flow mode (example 5) shows, that conversion and purity obtained under flow conditions (82% with 77% rpa Δ-Farnesene) are at least as good if not even better than the ones obtained under batch conditions (77% with 70% rpa Δ-Farnesene).

Example 7

Cyclopropanation reaction under flow conditions at 0.065% catalyst/substrate ratio and with batch-(example 1)-related addition mode as set forth in FIG. 3:

Equipment: as in example 2 but two microreactors (instead of one) and three pumps (instead of two).

Feed A: Farnesene of 98% purity (6.3 g, 31 mmol), Pd(acac)$_2$ (6.2 mg, 0.02 mmol. 0.065 mol %) in toluene (13 ml) pumped with 1.5 ml/min. Feed B: 3.5 M aqueous KOH (34 ml, 118 mmol) pumped with 2.2 ml/min. Feed C: Liquizald 33.5% in toluene (24.9 g) and toluene (1 ml) pumped with 1.9 ml/min.

Feed A (from reservoir 301) and feed B (from reservoir 302) are pumped (pumps 311 and 312) through the set-up of FIG. 3 into the first microreactor (321, mrx 1), where a biphasic mixture is preformed. From the first microreactor the flow (3.7 ml/min) is directed into the second microreactor (322, mrx 2) where it is combined with feed C (from reservoir 303) which is pumped (pump 313) with 1.9 ml/min into the second microreactor 322. From mrx 2 the flow is directed into the residence coil 331 from which the product flow (5.6 ml/min) is quenched (in vessel 341) sub-surfacely and under cooling (at 10-20° C. inner temperature through acetic acid (15 g, 0.25 mol). Work-up as described in example 2 gives a mixture (7 g) of unconverted Farnesene and crude Δ-Farnesene as a brown oil with a purity of 47%, as determined by GC- and NMR-calibration. GC of this material indicates Farnesene (44% rpa), Δ-Farnesene (56% rpa) and traces of Liquizald and Δ$_2$-Farnesene. Yield of Δ-Farnesene from Farnesene (corrected by purity): 48%.

This experiment shows that an addition mode as in batch example 1 which adds Liquizald to a preformed 2-phase mixture of Farnesene, Pd(acac)$_2$ in toluene and KOH in water, has two main disadvantages under flow conditions:
- a higher complexity (more pumps and microreactors)
- a significantly lower conversion (56% instead of 100%) of Farnesene which is probably due to pumping of an inhomogeneous mixture (feed A+feed B) into the second microreactor.

Example 8

Cyclopropanation reaction under flow conditions at 0.02% catalyst/substrate ratio and with batch-(example 1)-related addition mode as set forth in FIG. 3:

Feed A: Farnesene of 98% purity (6.4 g, 31 mmol) and Pd(acac)$_2$ (1.9 mg, 0.02 mmol, 0.02 mol %) in toluene (13 ml) pumped with 0.74 ml/min. Feed B: 3.5 M aqueous KOH (34 ml, 118 mmol) pumped with 1.1 ml/min. Feed C: Liquizald 39% in toluene (21.3 g) and toluene (5 ml) pumped with 0.96 ml/min.

The flow reaction described in example 7 was carried out with the same equipment set-up but with slightly changed feeds and with 2 mg (6.4 µmol, 0.02 mol %) Pd(acac)$_2$ instead of 6.2 mg (0.02 mmol, 0.065 mol %). Work-up as described in example 2 gave a mixture (7 g) of unconverted Farnesene and crude Δ-Farnesene as a brown oil with a purity of 43%, as determined by GC- and NMR-calibration. GC of this material indicates Farnesene (47% rpa), Δ-Farnesene (50% rpa), Δ$_3$-Farnesene (3% rpa) and traces of Δ$_2$-Farnesene and Liquizald. Yield of Δ-Farnesene from Farnesene (corrected by purity): 44%.

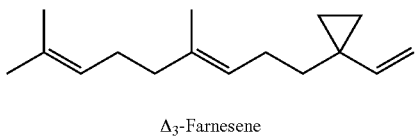 [SMILES: C=CC1(CC/C=C(\C)CCC=C(C)C)CC1]

Δ$_3$-Farnesene

This experiment shows similar effects as in example 7 at lower catalyst concentrations.

Example 9

A multistep flow experiment as set forth in FIG. 4.

Equipment: as in the flow reaction described in Example 2 (and represented by FIG. 1) but with some additional devices:
- five additional feeding pumps (total seven)
- 6 peristaltic pumps
- 3 additional T-connections (total 4)
- two plug flow reactors (pfr)
- five additional reservoirs for additional reagents, reactants and solvents (total seven)
- four CSTR's (continuously stirred tank reactors) with biphasic settlers
- 2 back pressure regulators Pumps, T-connections, microreactors, plug flow reactors and CSTR's are connected by teflon tubings. The T-connections are also made of teflon and are, for example, available from Sigma-Aldrich (Merck). The plug flow reactors are 1.25 m stainless steel tubes. The residence coil filled with static mixers is described in example 2.

Feed A: mesityl oxide (700 g, 7 mol). Feed B: methyl amine 40% in water (580 ml, 7.5 mol). Feed C: acid (11.4 mol) in 700 ml toluene. Feed D: NaNO$_2$ (543 g, 7.6 mol) in water (820 ml). Feed E: base 25% in water (1400 ml). Feed F: Farnesene (640 g, 3 mol) and Pd(acac)$_2$ (0.2 mg, 0.65 mmol. 0.02 mol %) in toluene (550 ml). Feed G: 3.5 M aqueous KOH (3400 ml, 11.7 mol). Flow rates, residence times and tube diameters are omitted for clarification.

Feed A (from reservoir 401) and feed B (from reservoir 402) are pumped (pumps 411 and 412) through the set-up of the scheme above into T-connection T$_1$ (491) and the first plug flow reactor (451, pfr$_1$) where these reactants undergo Michael addition to the mesityloxide methylamine adduct (MOMA), which is directed into T-connection T$_2$ (492), where acid in toluene (from reservoir 403, through feed C) and NaNO$_2$ in water (rom reservoir 404, through feed D) are subsequently added through two pumps (413, 414). After acidic nitrosation in the T-connection T$_3$ (493) and second plug flow reactor (452, pfr$_2$) the resulting Liquizald in a biphasic mixture in toluene and water is fed into a first CSTR (461a, continuously stirred tank reactor) and a biphasic settler (461b), where the phases are separated into an acidic waste water stream (passing a back pressure regulator 471) and a Liquizald stream in toluene, which is fed into the next three CSTR's (462a, 463a, 464a) and the corresponding biphasic settlers (462b, 463b, 464b) by several peristaltic pumps. Washing is affected with aqueous base (from reservoir 405, feed E) which is pumped (pump 415) countercurrently from the fourth CSTR (464a) and its biphasic settler (464b) via third CSTR (463a) and its biphasic settler (463b) to the second CSTR (462a) from which the basic waste water stream is discarded passing the biphasic settler (462b) and a back pressure regulator 472. A stream of essentially acid-free Liquizald in toluene is directed (pump 416) from the biphasic settler 464b of CSTR 4 (464a) to T-connection T$_4$ (494). Concomitantly, Farnesene and catalytic Pd(acac)$_2$ (from reservoir 406, feed F) are pumped (pump 417) into T-connectionT$_4$ (494) giving a homogeneous organic stream which is directed into microreactor (421) and residence unit (431) rc$_3$ filled with static mixers. Concomitantly, homogeneous aqueous base (from reservoir 407, feed G) is pumped (pump 418) into the microreactor (421) and residence unit (431, rc$_3$). After cyclopropanation reaction at 60° C. in the microreactor and residence unit filled with static mixers the product is quenched sub-surfacely (vessel 441) and under cooling through acetic acid (1.5 kg, 22.5 mol) The biphasic quench mixture is separated, the organic phase washed with water (10 l) dried azeotropically and evaporated under reduced pressure. Crude Δ-Farnesene (600 g) is obtained as brown oil with a purity of 80% (GC rpa) containing Δ$_2$-Farnesene (3% rpa) and unconverted Farnesene (16% rpa). Yield of Δ-Farnesene from Farnesene (corrected by purity): 78%. The crude product is further purified by distillation.

We claim:

1. A process for the continuous production of a reaction product of a diazo compound and a substrate in a multi-stage continuous flow reactor comprising at least two connected reactors in fluid communication with each other, wherein a reaction product formed at each stage of the multistage sequence is continuously discharged from an upstream reactor in which it is formed, and is fed as a continuous fluid stream into a downstream reactor whereupon it can undergo further conversion, the process being characterized in that a precursor compound of the diazo compound that is continuously formed in an upstream reactor is continuously discharged into a downstream reactor under conditions conducive to convert it into the diazo-compound, and wherein said downstream reactor contains the substrate with which the diazo-compound reacts to form the reaction product of the diazo compound and the substrate.

2. The process according to claim 1, wherein the diazo-compound is selected from the group consisting of diazoalkanes, diazocarboxylates, and combinations thereof.

3. The process according to claim 1, wherein the substrate is selected from the group consisting of olefins, aldehydes, ketones, cyclic ketones, carboxylic acids, acid chlorides, and combinations thereof.

4. The process according to claim 3, wherein the substrate is an olefin selected from di- or polyolefins.

5. The process according to claim 3, wherein the olefin is selected from the group consisting of isoprene, myrcene, farnesene, β-springene, and combinations thereof.

6. The process according to claim 1, wherein the diazo compound precursor is an N-alkyl-N-nitroso compound selected from the group consisting of N-methyl-N-nitroso urea (MNU), N-Methyl-N-nitroso-p-toluenesulfonamide, methyl N-methyl-N-nitroso carbamate, ethyl N-methyl-N-nitroso carbamate, N-methyl-N-(2-methyl-4-oxopentan-2-yl)nitroso amide, and combinations thereof.

7. The process according to claim 1, wherein the diazo compound is diazomethane, the substrate is an olefin and their reaction product is a cyclopropanated compound.

8. The process according to claim 7, wherein the diazomethane precursor compound formed in the upstream reactor is mixed with the olefin substrate, a catalyst and an organic solvent to form an organic phase, and this organic phase is mixed with an aqueous phase containing base to form a biphasic reaction mixture, which reaction mixture reacts to form the cyclopropanated compound in the downstream reactor.

9. The process according to claim 8, wherein the diazomethane precursor compound formed in the upstream reactor is contained in the organic phase of a biphasic mixture, and wherein the organic phase containing the diazomethane precursor compound is separated from the aqueous phase of the biphasic mixture before being mixed with an olefin substrate, catalyst and organic solvent.

10. The process according to claim 7, comprising the steps of:
providing a multi-stage continuous flow reactor comprising at least two connected reactors in fluid communication with each other;
at each stage of the reaction, continuously feeding a fluid stream of reactants in a directed flow into a reactor under conditions conducive to form a reaction product; continuously discharging from that reactor a fluid stream of reaction product, and feeding it into a successive reactor there to undergo further conversion to form a successive reaction product; characterized in that the diazomethane precursor compound formed as a reaction product in a reactor is continuously fed into a successive reactor under conditions conducive to convert the precursor compound into diazomethane, and wherein said successive reactor contains a the olefin substrate with which the diazomethane reacts to form the cyclopropanated compound.

11. The process according to claim 10, wherein the diazomethane precursor compound, discharged from the reactor is mixed continuously with the catalyst, substrate and solvent to form an organic phase, and this organic phase is mixed and reacted continuously with an aqueous phase containing a base in the successive reactor thereby to form the cyclopropanated compound.

12. The process according to claim 1 carried out under flow conditions.

13. The process according to claim 12, wherein the reaction is carried out in a microreactor.

14. The process according to claim 2, wherein the diazoalkane comprises at least one of diazomethane or diazoethane.

15. The process according to claim 2, wherein the diazocarboxylate comprises diazoacetate.

16. The process according to claim 4, wherein the substrate is an olefin selected from di- or polyolefins having at least one terminal (mono-substituted) double bond.

17. The process according to claim 11, wherein the base comprises KOH.

18. The process according to claim 10, wherein the multi-stage continuous flow reactor comprises at least three connected reactors in fluid communication with each other.

19. The process according to claim 10, wherein the multi-stage continuous flow reactor comprises at least four connected reactors in fluid communication with each other.

* * * * *